(12) United States Patent
Prisco

(10) Patent No.: US 8,183,520 B2
(45) Date of Patent: May 22, 2012

(54) OPTICAL FIBER SHAPE SENSOR CALIBRATION

(75) Inventor: Giuseppe Maria Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 383 days.

(21) Appl. No.: 12/618,000

(22) Filed: Nov. 13, 2009

(65) Prior Publication Data

US 2011/0113852 A1    May 19, 2011

(51) Int. Cl.
*G01J 1/04* (2006.01)
(52) U.S. Cl. .............. 250/227.14; 250/227.16
(58) Field of Classification Search ........... 250/227.14–227.23, 214 R, 559.1; 385/12, 13, 123–126; 74/490.01; 356/73.1, 356/435
See application file for complete search history.

(56) References Cited

U.S. PATENT DOCUMENTS

| | | | |
|---|---|---|---|
| 5,798,521 A | 8/1998 | Froggatt | |
| 6,389,187 B1 | 5/2002 | Greenaway et al. | |
| 7,781,724 B2 * | 8/2010 | Childers et al. | 250/227.14 |
| 2006/0013523 A1 | 1/2006 | Childlers et al. | |
| 2007/0156019 A1 | 7/2007 | Larkin et al. | |
| 2009/0324161 A1 | 12/2009 | Prisco | |
| 2010/0125284 A1 | 5/2010 | Tanner et al. | |

FOREIGN PATENT DOCUMENTS

WO    WO2008131303 A2    10/2008

OTHER PUBLICATIONS

Rice, Trevor, "NASA-Inspired Shaped-Sensing Fibers Enable Minimally Invasive Surgery," 2 pages, posted Feb. 1, 2008, Internet: http://www.techbriefs.com/content/view/2585.
Duncan, Roger G. et al., "Characterization of a Fiber-Optic Shape and Position Sensor," Proc. of SPIE, 2006, pp. 616704-1-616704-11, vol. 6167, SPIE.
PCT/US10/55566 International Search Report and Written Opinion of the International Searching Authority, mailed May 19, 2011, 17 pages.

* cited by examiner

*Primary Examiner* — Que T Le

(57) ABSTRACT

Calibration methods and apparatuses for a shape sensing optical fiber are disclosed. Strain is sensed in an optical fiber that is associated with a kinematic chain, and information derived from the sensed strain is used to determine a calibration relationship between the fiber and the kinematic chain. The strain may be sensed at a plurality of angles between two links in the kinematic chain. The strain may be sensed in a segment of the optical fiber that is associated with a joint in the kinematic chain as the joint sweeps through an arc. The strain may be sensed for the optical fiber in a known, predefined bend shape. The calibration information is stored in memory for later use during operation of the kinematic chain, so that shape information from the optical fiber can be used to accurately indicate the shape or pose of the kinematic chain.

48 Claims, 8 Drawing Sheets

OPTICAL FIBER SHAPE SENSOR CALIBRATION

BACKGROUND

1. Field of Invention

Inventive aspects are associated with optical fiber shape sensing, more particularly to calibrating an optical fiber shape sensor to a kinematic chain, and still more particularly to calibrating an optical fiber shape sensor to steerable device in a telerobotic surgical system.

2. Art

Optical fiber shape sensors are known. See e.g., U.S. Pat. No. 5,798,521 (filed Feb. 27, 1997) (disclosing "Apparatus and Method for Measuring Strain in Bragg Gratings"), U.S. Pat. No. 6,389,187 B1 (filed Jun. 17, 1998) (disclosing "Optical Fiber Bend Sensor"), U.S. Patent Application Pub. No. US 2006/0013523 A1 (filed Jul. 13, 2005) (disclosing "Fiber Optic Position and Shape Sensing Device and Method Relating Thereto"), and Roger G. Duncan et al., *Characterization of a Fiber-Optic Shape and Position Sensor*, Smart Structures and Materials 2006: Smart Sensor Monitoring Systems and Applications (D. Inaudi et al. eds.), 6167 Proceedings of SPIE 616704 (Mar. 16, 2006), all of which are incorporated herein by reference. Optical fiber shape sensors have been used to sense joint angles in a minimally invasive surgical instrument. See e.g., U.S. Patent Application Pub. No. US 2007/0156019 A1 (filed Jul. 20, 2006) (disclosing "Robotic Surgery System Including Position Sensors Using Fiber Bragg Gratings") and NASA Tech Briefs, *NASA-Inspired Shape-Sensing Fibers Enable Minimally Invasive Surgery* (Feb. 1, 2008), http://www.techbriefs.com/content/view/2585/ (last viewed Mar. 18, 2008), both of which are incorporated herein by reference.

When an optical fiber shape sensing system is used to determine the shape of a movable mechanical structure, and the shape information from the optical fiber is used to accurately place the mechanical structure in various poses in two or three dimensions, it is necessary to calibrate the fiber's reference frame to the mechanical structure's reference frame. Further, it is desirable to establish other useful relationships between the optical fiber and the mechanical structure that can be used to enhance control of the mechanical structure.

SUMMARY

In accordance with various inventive aspects, calibration methods and apparatuses for a shape sensing optical fiber are disclosed.

In one aspect, a multicore optical fiber is associated with a kinematic chain. Strain is sensed in a segment of the optical fiber. A reference frame is defined for the fiber, and another reference frame is defined for the kinematic chain. The sensed strain information is used to determine a calibration relationship between the fiber's reference frame and the kinematic chain's reference frame. The calibration relationship is stored in a memory for use when operating the kinematic chain, so that shape information from the optical fiber can be used to accurately indicate the shape or pose of the kinematic chain.

In another aspect, a segment of a shape sensing optical fiber extends between two links in a kinematic chain. The links are positioned at various angles with reference to one another, and the segment is interrogated for shape information. The shape information is then correlated with a reference frame defined for the kinematic chain to produce calibration information. The calibration information is stored in a memory for use when operating the kinematic chain. In one implementation, an actuator sweeps one of the links through an arc to produce the various angles, and the fiber segment is interrogated for shape information during the sweep, and the resulting shape information is sampled to be used for determining the calibration information.

In yet another aspect, a segment of a shape sensing optical fiber that is placed in a known, predefined shape and is interrogated for shape information. The shape information is correlated with a reference frame associated with a kinematic chain to produce calibration information. The calibration information is stored in a memory for use when operating the kinematic chain.

In still other aspects, various calibration apparatuses are disclosed that may be used to carry out calibration between a shape sensing optical fiber and a kinematic chain.

These and other inventive aspects are disclosed in more detail below.

DETAILED DESCRIPTION

Figure 1:
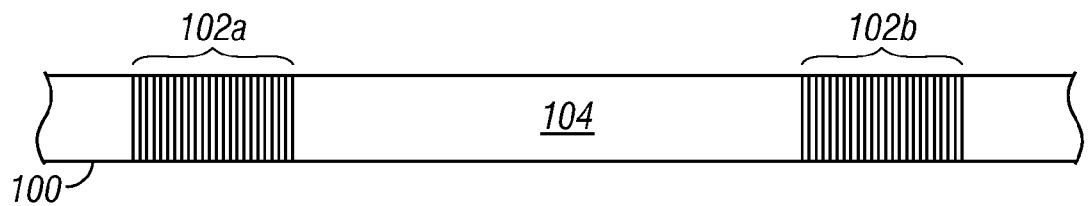
FIG. 1 is a diagrammatic view of an optical fiber core portion.

This description and the accompanying drawings that illustrate aspects and embodiments of the present invention should not be taken as limiting—the claims define the protected invention. Various mechanical, compositional, structural, electrical, and operational changes may be made without departing from the spirit and scope of this description and the claims. In some instances, well-known circuits, structures, and techniques have not been shown in detail in order not to obscure the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

The term "flexible" in association with a mechanical structure or component should be broadly construed. In essence, it means the structure or component can be bent without harm. For example, a flexible mechanical structure may include a series of closely spaced components that are similar to "vertebrae" in a snake-like arrangement. In such an arrangement, each component is a short link in a kinematic chain, and movable mechanical constraints (e.g., pin hinge, cup and ball, and the like) between each link may allow one (e.g., pitch) or two (e.g., pitch and yaw) degrees of freedom (DOF) of relative movement between the links. As another example, a flexible mechanical structure may be continuous, such as a closed bendable tube (e.g., nitinol, polymer, and the like) or other bendable piece (e.g., kerf-cut tube, helical coil, and the like). Accordingly, a short, flexible structure may serve as, and be modeled as, a single mechanical constraint (joint) providing one or more DOFs between two links in a kinematic chain, even though the structure itself may be a kinematic chain made of several coupled links.

FIG. 1 is a diagrammatic view of an optical fiber core portion 100. For clarity, the surrounding cladding, buffer layer, and fiber jacket are omitted from the various drawings. In addition, skilled artisans will understand that for all embodiments, core and associated fiber structure dimensions may be tailored using known design principles to carry light of a specific wavelength or to meet other physical design requirements. In FIG. 1, two fiber Bragg gratings (FBG's) 102a,102b are shown formed in fiber core portion 100. FBG's 102a,102b are illustrative of many such FBG's typically formed along the full length of a core. The many vertical lines shown in each FBG 102 represent the changes in refractive index that characterize an FBG. As shown in FIG. 1, FBG's 102a,102b are separated by a tether segment 104, which is completely transmissive. The lengths of the various FBG's 102 and tether segments 104 may be selected according to various design requirements, and so these lengths are established for subsequent calculation.

As is known, each of the FBG's 102 may be interrogated for strain information. In a fiber that contains two or more cores arranged side-by-side, with FBG's in each core positioned adjacent one another across the fiber, the fiber's bend direction may be determined by the difference in strain between each adjacent FBG (minimum of two adjacent FBG's for planar bend; minimum of three adjacent FBG's for volumetric (an arbitrary spatial) bend). The relative strain information from each core is compared at each FBG location, and the known tether segment length (e.g., 5 mm) is used to estimate the position of the next FBG location. In this way, the fiber shape associated with the interrogated FBG's may be determined. Such bend information may be used in forward kinematic calculations to determine the position of the distal end of a kinematic chain (e.g., a minimally invasive surgical instrument).

Figure 2:
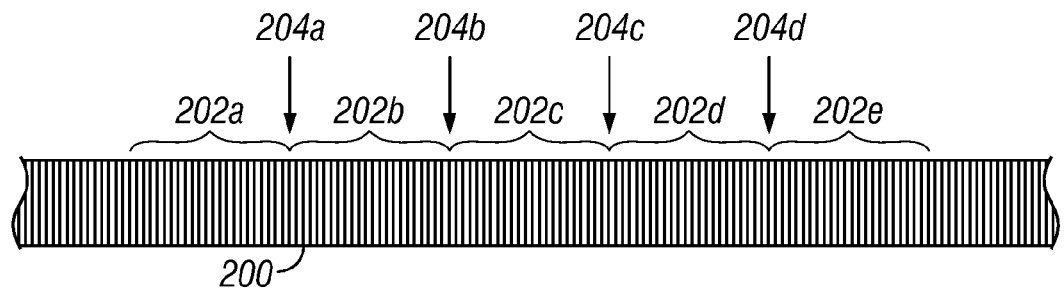
FIG. 2 is a diagrammatic view of another optical fiber core portion.

FIG. 2 is a diagrammatic view of another optical fiber core portion 200. Core portion 200 shows illustrative FBG's 202a-202e formed adjacent one another along the optical fiber core. There are no tether segments between the FBG's. In some instances a boundary region, illustrated by regions 204a-204d, separates adjacent FBG's such that the spacing between the refractive index changes in each ERG 202a-202e may not be exactly the same as the spacing between FBG's. Consequently, the FBG's 202 are formed continuously, or effectively so, in the fiber core. Again, the many vertical lines shown in each FRG 202 represent the changes in refractive index that characterize an FBG. Aspects of the invention use fiber core embodiments as shown in FIG. 2, although other fiber core embodiments (e.g., FBG's as shown in FIG. 1 that are spaced to obtain useful bend information for calibration) may be used.

Bend Information

Figure 3:
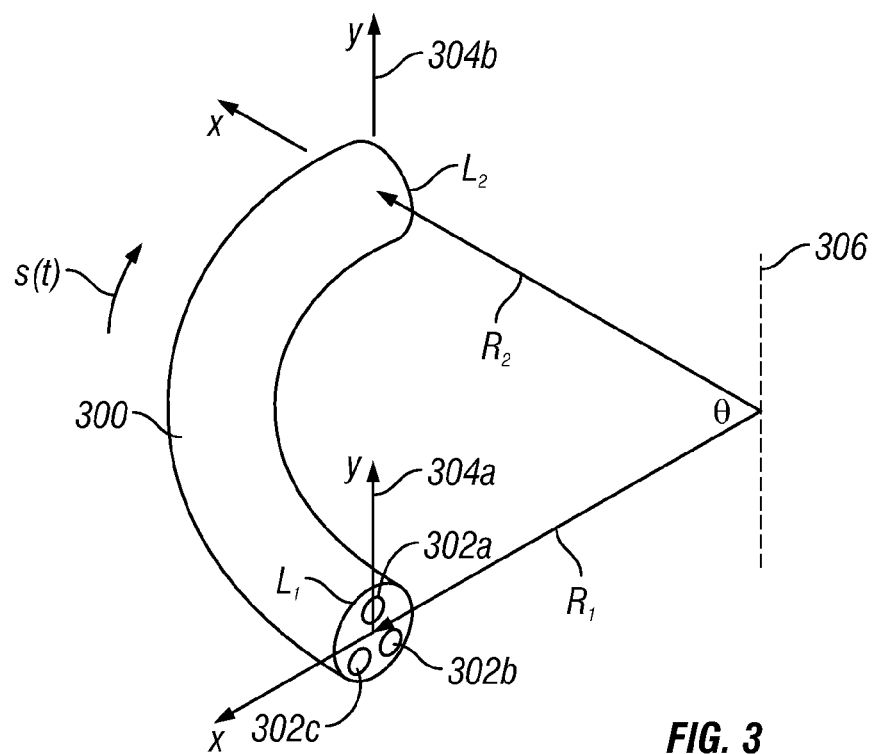
FIG. 3 is a diagrammatic view of a portion of an optical fiber shape sensor.

FIG. 3 is a diagrammatic view of a portion 300 of an optical fiber shape sensor. As shown in FIG. 3, three illustrative cores 302a-302c are equidistantly spaced around the fiber's center longitudinal (extending between proximal (nearest the base) to distal ends) axis. In one aspect the cores are configured with FBG's as described above with reference to FIG. 2. Differential strain information among the cores 302a-302c is used to determine bend in the fiber.

As indicated in FIG. 3, a curvilinear coordinate system s(t) is defined for the fiber along its longitudinal axis. The origin of the curvilinear coordinate system may be defined at various locations (e.g., at the proximal end of the fiber, at a particular distance along the fiber, at the distal end of the fiber, and the like). The direction of the curvilinear coordinate system may be defined so that either the s coordinate of a point increases or decreases as the point is moved towards the distal tip of the fiber.

Each location along the curvilinear coordinate system defined for the fiber has an intrinsic two-dimensional (2-D) reference frame. As shown in FIG. 3, for example, 2-D reference frame 304a (an illustrative conventional orthogonal xy-axis frame is shown) exists at curvilinear location $L_1$. Likewise, a similar 2-D reference frame 304b exists at curvilinear location $L_2$. As shown in FIG. 3, one of the axes (e.g., the y-axes) of the reference frames is consistently defined to intersect one of the cores (e.g., core 302a). Defining the reference frames with respect to a common core simplifies differential strain calculation in a multicore fiber.

The differential strain information at each sensed location on the fiber is used to determine the bend radius and the bend axis for that location in the frame 304 for that location. As shown in FIG. 3, for instance, location $L_1$ has a location bend radius $R_1$ and location bend axis 306 determined in frame 304a. Similarly, location $L_2$ has location bend radius $R_1$ and location bend axis 306 determined in frame 304b.

The fiber illustrated in FIG. 3 is bending with a constant radius in a plane, and so $R_1$ and $R_2$ are equal, and both locations $L_1$ and $L_2$ have the same bend axis 306. In other situations, however, the fiber bend may not be consistent, and various locations may have different bend radii and bend axes. Nevertheless, in both constant bend radius and varying bend radius conditions for a particular fiber segment defined between two locations, the curvature and bend axis at each sensed location may be integrated over the length of the fiber segment between the locations to determine (i) the total bend angle θ of the fiber segment, and (ii) a common bend axis for the bend. Such integration may be carried out by using methods described in U.S. patent application Ser. No. 12/164,829 (filed Jun. 30, 2008) (disclosing "Fiber Optic Shape Sensor"), which is incorporated herein by reference.

Figure 4:
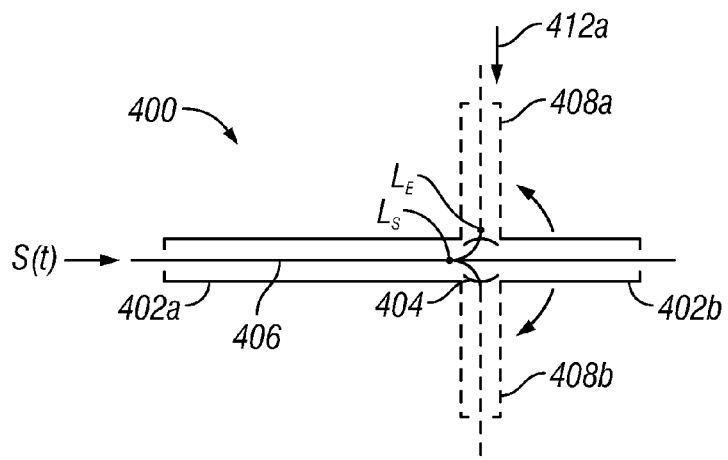
FIG. 4 is a schematic view of a kinematic chain.

FIG. 4 is a schematic view of a kinematic chain 400 made of a proximal link 402a and a distal link 402b coupled by a single degree of freedom (DOF) revolute joint 404, which is illustrative of various movable mechanical constraints of one or more DOF's (e.g., prismatic, cylindrical, screw, planar, spherical, etc.) that may couple the two links 402a,402b to allow various relative movements. Joint 404 allows distal link 402b to move in a single plane with reference to link 402a. A shape sensing optical fiber 406 is routed through proximal link 402a, through joint 404, and through distal link 402b. As shown in FIG. 4, in some embodiments the fiber is positioned along the centerlines of links 402a,402b (e.g., embedded in a PTFE tube that is placed in a central bore in the links). In this illustrative embodiment, fiber 406 is a three core optical fiber as described above. In other embodiments, various numbers of cores may be used to sense bend due to differential strain measurements.

Figure 4A:
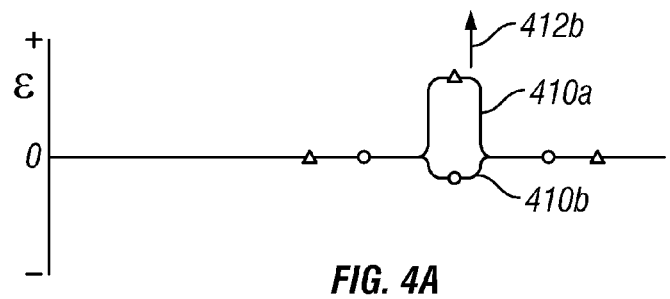
FIGS. 4A and 4B are illustrative, simulated graphical plots of two differential strain measurements from cores in an optical fiber.
Figure 4B:
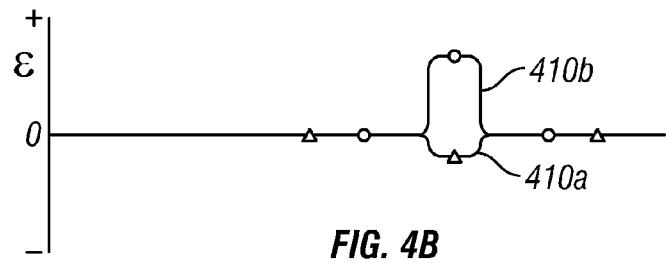

FIGS. 4A and 4B are illustrative, simulated graphical plots of two differential strain (ε) measurements from fiber 406 (FIG. 4). When distal link 402b is moved to a first alternate pose 408a, strain occurs in the portion of fiber 406 that bends. As shown in FIG. 4A, a first differential strain 410a (indicated by triangles) is plotted and shown as having a positive value in the portion of fiber 406 that bends. An example of such a positive value is a strain difference between core 302c and core 302a as shown in FIG. 3—core 302a is functioning as a reference core—because the fiber is bending away from core 302c. Similarly, a second differential strain 410b (indicated by circles) is plotted and shown as having a negative value in the portion of fiber 406 that bends. An example of such a negative value is a strain difference between core 302b) and core 302a as shown in FIG. 3, because the fiber is bending towards core 302b. There are no strain differences in the portions of fiber 406 that do not bend inside links 402a,402b. When distal link 402b is moved in an opposite direction to a second alternate pose 408b, strain in the portion of fiber 406 that bends is reversed. As shown in FIG. 4B, the first differential strain 410a now has a negative value and the second differential strain 410b now has a positive value.

The start and end locations of the portion of the fiber that bends are defined in the curvilinear coordinate system s(t) defined for the fiber. The origin of s(t) may be at the proximal end of the fiber or at another location along the fiber. As shown in FIGS. 4 and 4A, for example, the curvilinear location at which differential strain begins to be sensed corresponds to start location $L_S$ on fiber 406, and the curvilinear location at which differential strain is no longer sensed corresponds to location $L_E$ on fiber 406. Accordingly, a bend sensing segment in fiber 406 that is associated with joint 404 may be defined between start location $L_S$ and end location $L_E$.

To account for real world conditions that may affect the fiber, such as temperature changes or mechanical tolerances in the joint, the bend sensing segment may be defined to start proximally of $L_S$ and/or to end distally of $L_E$. A similar adjustment is required if the fiber slides in relation to one or both links as the joint moves.

In some cases, the centerline of fiber 406 may not match a perfect geometric curve between the two links as the joint bends. If the fiber is affixed (e.g., glued, clamped, and the like) to both links, then the start and end locations will not vary. If the fiber is affixed to only one link, or is not affixed to either link, then the fiber may slide with reference to one or both links. For example, if the fiber is affixed to proximal link 402a, then fiber 406 may slide in a proximal direction in relation to distal link 402b as it moves to alternate pose 408a, as shown by arrow 412a. Likewise, fiber 406 may slide proximally in relation to distal link 402b as distal link 402b moves to alternate pose 408b, as shown by arrow 412b. Or, fiber 406 may slide distally as the joint moves. And, such fiber sliding may be intentionally designed.

Figure 4C:
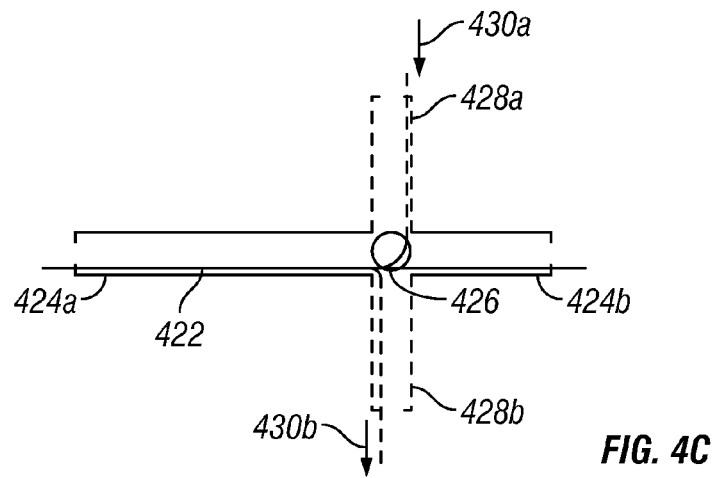
FIG. 4C is a schematic view of another kinematic chain.

In some cases, the fiber is positioned away from the kinematic chain's longitudinal centerline (e.g., to provide space in the kinematic chain's centerline bore). FIG. 4C is a schematic view of another kinematic chain 420, similar to chain 400, but with a shape sensing multicore optical fiber 422 positioned away from the centerlines of proximal link 424a and distal link 424b. FIG. 4C shows that as joint 426 rotates to move distal link 425b to various positions in its range of motion, illustrated by alternate positions 428a and 428b, fiber 422 slides because of the changing bend radii of the locations in the bending portion of fiber 422. As shown in FIG. 4C, if fiber 422 is fixed with reference to proximal link 424a, then fiber 422 slides proximally in relation to distal link 424b when distal link 424b moves generally away from the side to which fiber 422 is offset, as illustrated by arrow 430a. Similarly, fiber 422 slides distally in relation to distal link 424b when distal link 424b moves generally towards the side to which fiber 422 is offset, as illustrated by arrow 430b.

Therefore, for situations in which the fiber slides with reference to one or both links, the change in start and end locations for the bend information over the joint's range of motion indicate the length of sliding. The start location $L_S$ and the end location $L_E$ may be adjusted to account for the maximum fiber sliding. This adjustment may be based on sensing the extreme bend segment start and end locations over the joint's range of motion, on a predetermined curvilinear distance subtracted from a measured segment start location or added to a measured segment end location, or to a combination of both.

Calibration

In order for the optical fiber sensor to properly indicate the shape and position of its associated kinematic chain, the shape information from the fiber is calibrated to the kinematic chain. That is, the fiber reference frame is calibrated to the kinematic chain reference frame. Calibration may be done for each joint in each kinematic pair in a series of one or more kinematic pairs, or it may be done for a length that spans two or more joints in a series of kinematic pairs. Obtaining information for such calibration may be carried out in various ways, such as joint level calibration, three-dimensional (3-D) calibration, and self-calibration.

Joint Level Calibration

In one aspect, local bend information is collected for at least a portion of an optical fiber shape sensor that is associated with a single DOF joint (e.g., a segment as described above) as the joint is at various angles within its range of motion. The collected information is then used for calibration. For example, sensed optical fiber bend information is calibrated to a planar movement of a revolute joint in a kinematic pair. The local bend information is determined at various curvilinear locations along the shape sensing optical fiber associated with the joint. This local bend information is the curvature and bend radius at each sensed location, expressed in the location's 2-D reference frame, as described above. In some embodiments the revolute joint may have a single mechanical pivot. In other embodiments the revolute joint may be a flexible mechanical structure between the links in the kinematic pair. The flexible mechanical structure itself may be made of a series of joints (e.g., a "snake-like" series of small vertebrae), or it may be a continuously bending piece, and it may be modeled as a single joint.

In some instances the local bend information is obtained by sampling the local bend locations as an actuator (e.g., robotically controlled) changes the relative angle of the two links coupled by the joint from one angle to another angle. In other instances, an actuator moves the relative angle between the two links to various static angles, and the local bend information is obtained at each static angle. For either sampling local bend information during joint movement or at static angles, two arrays are produced. One array contains local bend radius values; the other, local bend axis values. The same local bend information can be equivalently represented as two arrays, one containing the local curvature (i.e., the inverse of bend radius) around the x-axis of the fiber local frame of reference, the other containing the local curvature around the y-axis of the fiber local frame of reference. The length of the arrays is equal to the number of sensed locations along the bend in the fiber. There is one set of the two arrays for each sample or static angle at which the local bend information is sensed.

A Denavit-Hartenburg (DH) frame is associated with the proximal link in the kinematic pair. The 3-D Cartesian orientation of this DH frame is determined from known mechanical dimensions. The DH frame's z-axis is defined to be aligned with the mechanical joint axis is defined for the DH frame. The joint angle is determined by, e.g., one or more encoders associated with one or more motors that are used to move the links relative to one another as constrained by the joint. Various other ways of determining the joint angle are possible, such as using optical triangulation technology, or using image-based position sensing (e.g., "tool tracking" technology as illustrated in U.S. Patent Application Pub. No. US 2009/0088897 A1 (filed Sep. 30, 2007) (disclosing "Methods and Systems for Robotic Instrument Tool Tracking"), U.S. patent application Ser. No. 12/428,691 (filed Apr. 23, 2009) (disclosing "Configuration Marker Design and Detection for Instrument Tracking"), and U.S. patent application Ser. No. 12/495,304 (filed Jun. 30, 2009) (disclosing "Efficient Vision and Kinematic Data Fusion for Robotic Surgical Instruments and Other Applications"), all of which are incorporated herein by reference).

Once the information from the optical shape sensor is collected, calibration associated with the kinematic pair may then occur. A first type of calibration that may be performed is to map the 2-D local bend axis at each sensed location to the joint's bend axis in the DH frame. This calibration is done by using a 2×2 rotation matrix (2-D) to transform the local bend axes into the joint's plane of movement. If the fiber twists as it extends along the segment, and such twist is constant at each sensing location as the joint bends, then the effect of twist can be taken into account (i.e., calibrated out) during the integration step (see next paragraph below) by knowing the local transformation between the (twisted) fiber reference frame and the joint reference frame.

A second type of calibration that may be performed is to define the joint's bend angle in terms of the local curvature information at each sensed local location. This is done by integrating the local curvature information over the number of locations, as described above. For example, various joint angle positions (e.g., 0°, ±10°, etc.) may be defined based on the fiber sensor information.

A third type of calibration that may be performed is to determine the locations along the fiber at which the bend starts and ends, as described above. This type of calibration identifies the corresponding joint and fiber bend locations. Once a correspondence between joint and fiber bend locations is established, shape information from the fiber sensor can be used to control the angle of the joint in a closed loop control system.

A fourth type of calibration that may be performed is for situations in which the fiber is offset from the kinematic chain's centerline. Since bend start and end locations can be determined for various joint angles, the amount of fiber sliding that occurs as the joint moves through an angle may be determined, and this information is used to determine the fiber's exact offset from the centerline.

Figure 5:
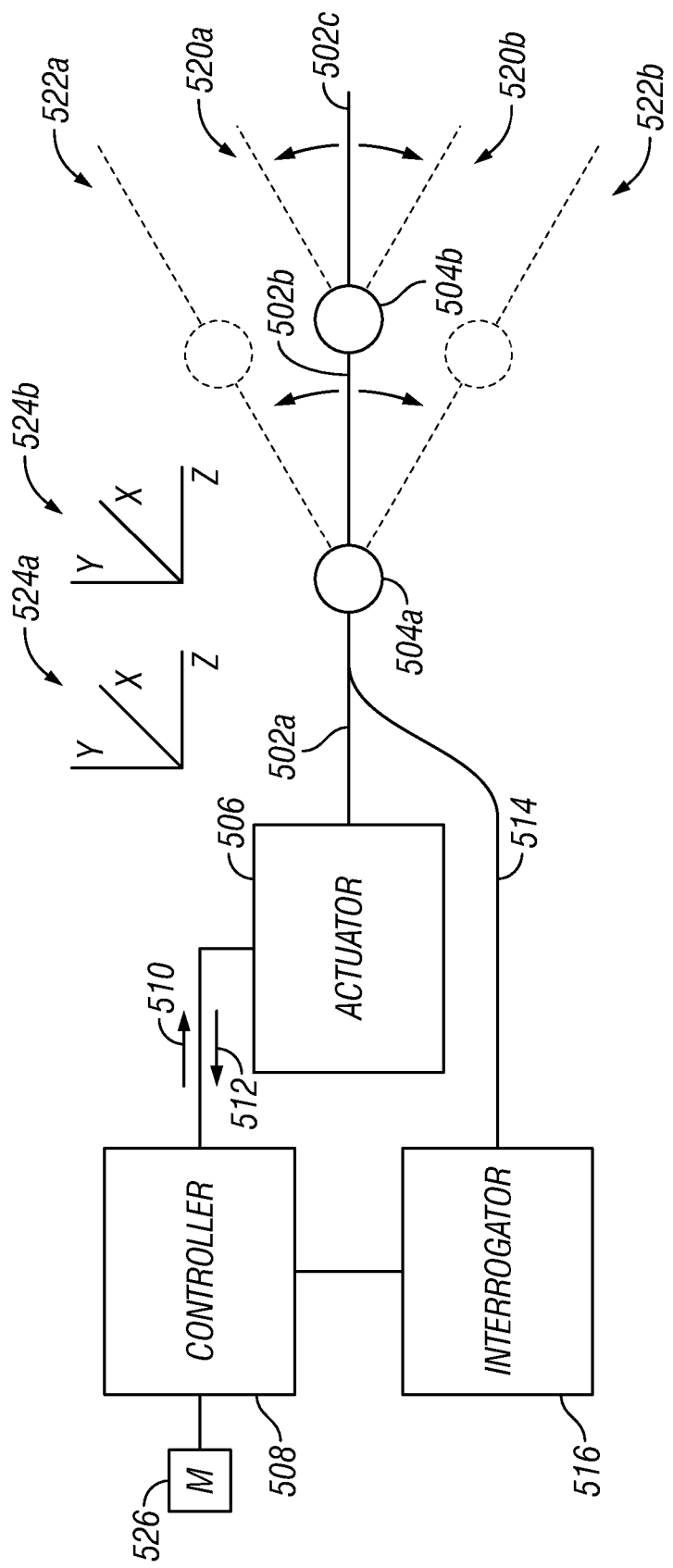
FIG. 5 is a schematic view of a kinematic chain with associated control, calibration, and shape sensing systems.

The following examples illustrate such "Joint Level Calibration". FIG. 5 is a schematic view of a serial kinematic chain of two kinematic pairs with associated control and shape sensing systems. The kinematic chain includes a first (proximal) link 502a, a second (middle) link 502b, and a third (distal) link 502c. A first revolute joint 504a couples links 502a and 502b, and a second revolute joint 504b couples links 502b and 502c. A servomotor actuator unit 506 controls movement of joints 504a and 504b via, e.g., cables that run through channels in the links 502. Actuator unit 506 is illustrative of various actuating motors (e.g., electrical, hydraulic, pneumatic, linear electric, shape memory alloy, polymer "artificial muscle", and the like) and mechanisms (e.g., cables, cable/hypotube assemblies, rods, and the like) that may be used. In the example shown in FIG. 5, actuator unit 506 operates under the control of controller 508. Signals 510 from controller 508 command servomotors in actuator unit 506 to move a designated amount, and in turn the servomotors move their associated part of the kinematic chain. Encoders for each servomotor send signals 512 that represent the motor's movement back to controller 508. Accordingly, controller 508 uses the kinematic chain's known physical dimensions and the motor encoder information to determine the kinematic chain's pose from forward and inverse kinematic calculations. Illustrative actuator units, controllers, and sensors are disclosed in U.S. Pat. No. 6,132,368 (filed Nov. 21, 1997) (disclosing "Multi-component Telepresence System and Method"), U.S. Patent No: U.S. Pat. No. 6,671,581 B2 (filed Jun. 5, 2002) (disclosing "Camera Referenced Control in a Minimally Invasive Surgical Apparatus"), U.S. Pat. No. 6,817,974 B2 (filed Jun. 28, 2002) (disclosing "Surgical Tool Having Positively Positionable Tendon-actuated Multi-disk Wrist Joint"), United States Patent Application Pub. No. US 2007/0156019 A1 (filed Jul. 20, 2006) (disclosing "Robotic Surgery System Including Position Sensors Using Fiber Bragg Gratings"), and U.S. patent application Ser. No. 12/164,829 (filed Jun. 30, 2008) (disclosing "Fiber Optic Shape Sensor"), all of which are incorporated herein by reference. Skilled artisans will be familiar with other robotic control and actuation devices and methods.

FIG. 5 further shows that a multicore fiber optic shape sensor 514, as described above, is associated with the kinematic chain. A portion of optical fiber 514 is embedded in the kinematic chain (i.e., in links 502a-502c), and a shape sensing strain interrogator 516 is coupled to the proximal end of optical fiber 514. In one embodiment, an interrogator unit supplied by Luna Innovations, Inc. is used to provide sensed strain information.

In some instances, the local bend information in fiber 514 may be sampled as an actuator sweeps a joint through an arc between a first angle and a second angle. Referring to FIG. 5, for example, local bend information for the portion of fiber 514 associated with joint 504a is sampled as actuator unit 506 sweeps joint 504a to alternate pose 522a. As described above, this local bend information is the bend radius and bend axis at each sensed location, expressed in the sensed location's 2-D coordinate system, defined in relation to the cores in the fiber. Equivalently, the local bend information is represented as the local curvature (the inverse of the bend radius) of the fiber around the x-axis and around the y-axis of the fiber 2-D coordinate system. To compute the calibration matrix that relates the local bend information to the kinematic chain frame of reference, the following procedure, with a simple graphical explanation, can be performed using, e.g., an electronic data processing system. First a joint of the kinematic chain is moved to a bend configuration, and then the local bend information for all the sensed locations along the segment is collected and plotted on a 2-D graph with the horizontal axis representing value of the local curvature (the inverse of the bend radius) of the fiber around the x-axis, and the vertical axis representing value of the local curvature (the inverse of the bend radius) of the fiber around the y-axis. Since the bend on the fiber is approximately planar, the plotted points will tend to align on line. The orientation of the line with respect to the x-axis (an angle value) is the amount of rotation between the local 2-D fiber reference frames and the reference frame of the joint of the kinematic chain. Such rotation (angle value) is the desired calibration data. The same procedure can be repeated for other joints of the same kinematic chain. An alternative approach to compute the calibration matrix that relates the bend information to the kinematic chain frame of reference is based on first performing the integration of the local 3-D bend information along the segment to compute the fiber segment tip position and orientation vector $\vec{V}$ (of unitary norm) with respect to the fiber segment base frame of reference for a set of known bend angles of the kinematic chain. The arctangent of the $$\frac{\vec{V}_x}{\vec{V}_z}$$

(i.e., the segment tip orientation angle x) and the arctangent of $$\frac{\vec{V}_y}{\vec{V}_z}$$

(i.e., the segment tip orientation angle y) are the angles between respectively the tip of the fiber and the x-axis of the fiber segment base frame of reference and the tip of the fiber and the y-axis of the fiber segment base frame of reference. The desired calibration data is the rotation that when applied to $\vec{V}$ makes the segment tip orientation angle x equal to the joint angle that is known in the calibration pose. An advantage of this second method is that it does not require the local bend information, but only their integrated values summarized by the fiber segment tip position and orientation vector $\vec{V}$, as described in U.S. patent application Ser. No. 12/164,829, cited above. It also supports the 3-D calibration described below.

Likewise, local bend information for the portion of fiber 514 associated with joint 504b is sampled as actuator unit 506 sweeps joint 504b to alternate pose 520a.

In other instances, an actuator positions the joint to various static angles. At each static angle, interrogator 516 determines local bend information for curvilinear locations in fiber 514 that are associated with the bend. For example, three sets of local curvature information for the portion of fiber 514 associated with joint 504a may be obtained by controller 508 commanding joint 504a to move to a straight pose, to alternate left angle pose 520a, and to alternate right angle pose 520b as shown. Likewise, three sets of local curvature information for the portion of fiber 514 associated with joint 504b may be obtained by controller 508 commanding joint 504b to move to a straight pose, an alternate left angle pose 522a, and to alternate right angle pose 522b as shown.

The sensed local bend information, as described above, may be stored in, e.g., a memory 526 associated with controller 508. Similarly, encoder information is stored in the memory. A DU frame 524a associated with link 502a and joint 504a is defined in the controller. A DH frame 524h associated with link 502h and joint 504b is likewise defined.

An electronic data processing unit associated with controller 508 then receives the sensed local bend information, joint angle information, a priori information about the kinematic chain (e.g., dimensions, angular relationships), and definitions (e.g., DH frames) and then outputs calibrations as described above. The local bend axis information from the fiber 514 segment associated with joint 504a is mapped to the joint 504a bend axis defined in DH frame 524a. Similarly, the local bend axis information from the fiber 514 segment associated with joint 504h is mapped to the joint 504b bend axis defined in DH frame 524h. The angular displacements of each joint are determined from local curvatures, segment start and end locations are determined for each segment associated with a joint, and fiber offset from centerline is determined, if applicable, at one or more portions of the kinematic chain.

This calibration allows controller 508 to use sensed bend information from fiber 514 to determine the pose of the links 502a-502c in the DH reference frame associated with the kinematic chain. And, controller 508 may use the difference between a commanded desired pose and the actual pose to output additional signals 510 to actuator unit 506 to move the links to the desired pose. Further, calibration information determined, e.g., during manufacturing, may be stored in a memory (e.g., memory 526) which may be associated with the kinematic chain. Such a memory may be in various locations, such as in a robotic base unit, a control system for a telerobotic system, or in the case of interchangeable robotic instruments, supplied with the particular kinematic chain for which the calibration information applies. The memory may be in one or more physical locations so that, e.g., a priori kinematic chain information is stored at one location and calibration information is stored at another location. Thus the depicted memory is illustrative of various memory systems. The kinematic chain and its calibration information may then be provided together, and another controller may access and use the stored calibration information to properly control the kinematic chain.

Calibration is described above in terms of a planar movement for a single DOF (e.g., pitch) revolute joint. It should be understood that a similar calibration may be done for a multi-DOF joint (e.g., spherical joint or flexible assembly that moves in pitch and yaw). For example, one calibration may be accomplished for joint movement in a first plane, and another calibration may be accomplished for joint movement in a second plane that is orthogonal to the first plane. Accordingly, two bending planes of a 2-DOF joint may be distinguished for control purposes.

3-D Calibration

In another aspect, calibration is accomplished by setting a kinematic chain in a known pose with a mechanical fixture. In this aspect, the bending segment associated with each joint is outputting Cartesian position and orientation for its end location. Rather than computing the 2-D rotation matrix as described above, a full 3-D rotation and translation matrix is computed using an approach similar to the description above.

Figure 6:
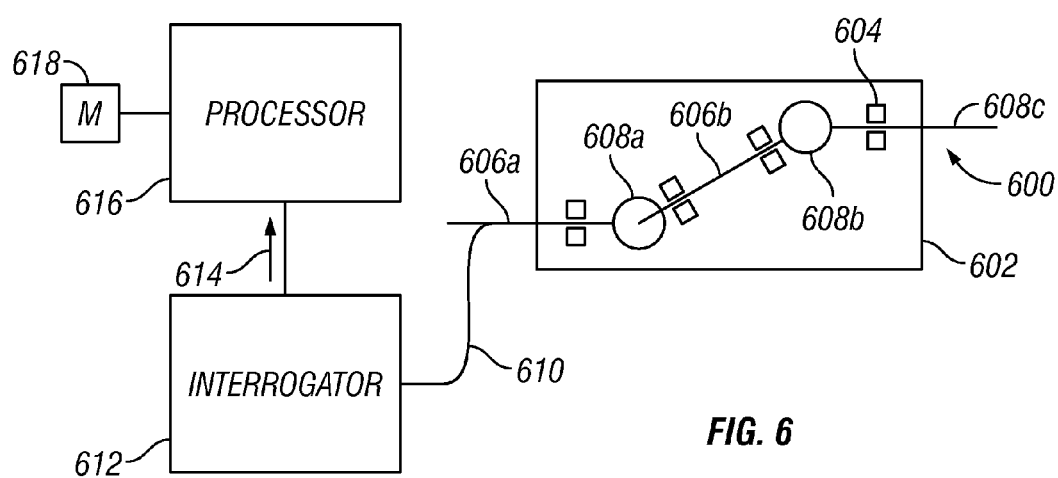
FIG. 6 is a schematic view of a kinematic chain, removably positioned in a mechanical jig, and associated shape sensing and calibration components.

FIG. 6 is a schematic view of a kinematic chain 600 removably positioned in a mechanical jig 602, and associated shape sensing components, for determining calibration information. Bosses 604 hold links 606a (proximal), 606b (middle), and 606c (distal) in known 2-D or 3-D orientations with reference to one another. An optical fiber 610 is embedded in chain 600 so that it senses the angles of joints 608a and 608b in 2-D or 3-D space. This bending is sensed by interrogator 612, which passes the position and orientation information from the fiber as signal 614 to electronic data processor 616. This position and orientation information can be calibrated to the known position and orientation of one or more portions of kinematic chain 600. In one situation, for example, a single bend segment may be defined in fiber 610 for joint 608a. Information from this bend segment may be calibrated to the known positions and orientation of links 606a and 606b. In another situation, for example, a single bend segment may be defined over two or more joints. Such a bend sensing segment may be defined to include both joints 608a and 608b so that the segment is used to determine position and orientation of link 608c with reference to link 608a.

Bend axis, joint angle, segment start and end locations, and fiber offset from centerline calibrations may be determined as described above. Calibration information may be stored for use in memory 618, similar to memory 525 (FIG. 5).

Figure 6A:
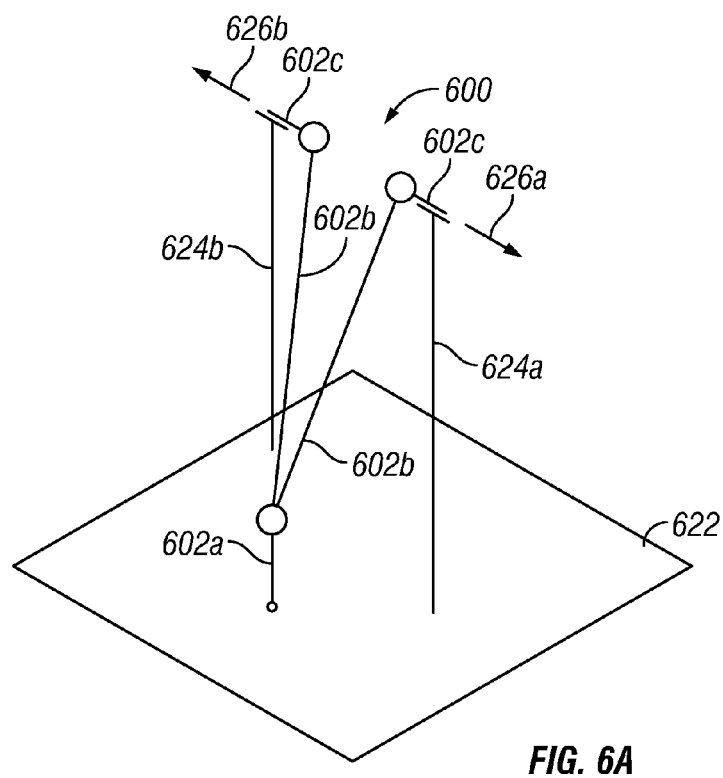
FIG. 6A is schematic view of a kinematic chain removably positioned in a mechanical jig.

FIG. 6A is schematic view of a kinematic chain 600 removably positioned in a mechanical jig 622 for determining calibration information. The arrangement shown in FIG. 6A is similar to the arrangement shown in FIG. 6, except that an illustrative 3-D fixture is specifically shown. As shown in FIG. 6A, distal link 602c is first positioned in jig fixture 624a so that it has a first position and orientation 626a. Distal link 602c is then positioned in jig fixture 624b so that it has a second position and orientation 626b. It can be seen, therefore, that various positions and orientations for the distal end of the chain (or a middle portion, if desired) can be established to collect calibration data.

As an alternative to positioning in a mechanical jig, each joint of the kinematic chain can be driven to its hardstop at the end of its range of motion, which is known exactly by design. The use of a jig is thus avoided.

It should be appreciated that although the kinematic chain 600 is illustratively shown as having three links, it may also be flexible. Thus a distal portion of a flexible structure may be placed in various known positions and orientations to obtain the necessary calibration information.

Self Calibration

Figure 7:
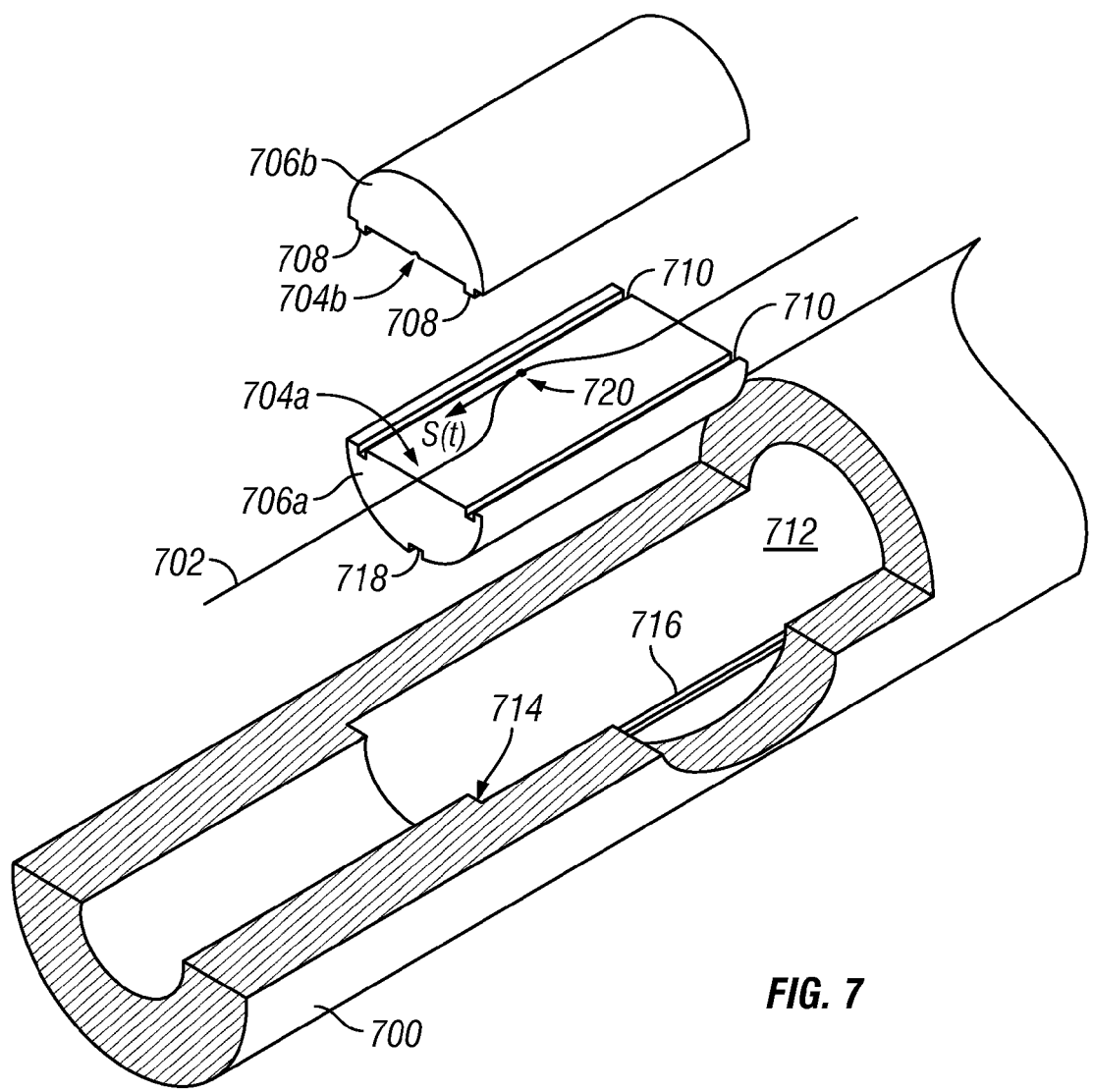
FIG. 7 is an exploded, diagrammatic, perspective, partial cutaway view of a link in a kinematic chain with an associated predefined shape in an optical fiber.

In yet another aspect, calibration is accomplished by fixing a bend having a predefined shape (known curvature pattern) in the shape sensing optical fiber at a predefined location in a kinematic chain. FIG. 7 is an exploded, diagrammatic, perspective, partial cutaway view of a link 700 in a kinematic chain. Link 700 may be the most proximal link in the chain, or it may be another link in the chain. Alternatively, positioning the bend in link 700 as depicted is illustrative of positioning the bend in a base for the kinematic chain. And so, link 700 is also illustrative of aspects that use a fixed bend in an optical fiber to define a reference frame, even though the fixed bend may not be directly associated with a kinematic chain. For instance, the bend may be used to define an earth reference frame for a kinematic chain, and it may be located outside the chain.

As shown in FIG. 7, an optical fiber 702 is embedded in link 700, which is an elongated tube. A planar groove 704a having known bend dimensions is defined (e.g., engraved, etched) in bottom fixture piece 706a. Fiber 702 is positioned in groove 704a so that it follows the groove's bend. A mirror image groove 704b is defined in top fixture piece 706b. When the bottom and top fixture pieces 706a,706b are brought together, the grooves 704a,704b form a narrow bore in which fiber 702 is positioned. The top and bottom fixture pieces 706a,706b are aligned with each other using keys 708 and slots 710. Fiber 702 may be held in position in grooves 704a,704b by, e.g., friction, glue, or any other suitable way of keeping the fiber from sliding.

The assembled fixture pieces 706a,706b and fiber 702 are assembled to link 700 so that the planar bend in the fiber is at a known orientation to link 700. FIG. 7 shows that the assembled fixture pieces 706a,706b are inserted into the central bore 712 in link 700 until they abut annular shoulder 714. As an example alignment mechanism, key 716 on the interior wall of bore 712 mates with groove 718 on bottom fixture piece 706a. Thus shoulder 714 and key 716 provide a translational and rotational reference for the planar bend in the fiber with reference to link 700.

As described above, differential strain information is interrogated at various locations in the segment of the multi-core fiber 702 associated with the planar bend. By reading the strain in the x-y reference plane defined at various locations in the section of the fiber over the planar bend in the fixture, a fixed 2-D rotation may be determined between the reference frame of the fiber cores and the reference frame of the fixture.

In addition, the planar bend may be used to define an origin of the curvilinear coordinate system s(t) for fiber 702. For example, the origin may be correlated to the middle point 720 of the constant bend in the fiber at which a tangent is parallel to the direction of the fiber as it exits the fixture, as shown in FIG. 7.

Figure 7A:
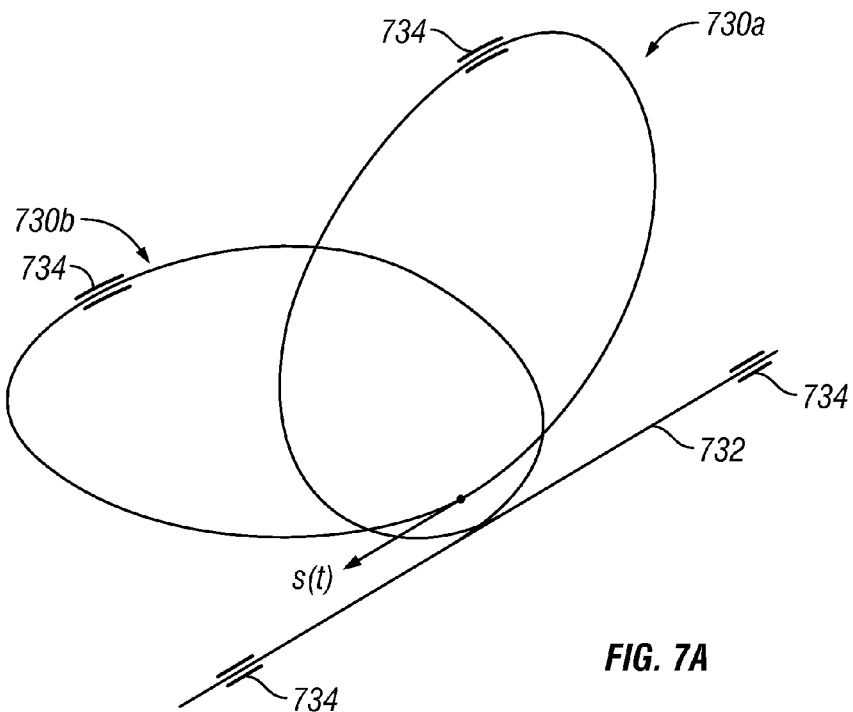
FIG. 7A is a diagrammatic perspective view that illustrates a more general implementation of a fixed fiber bend that may be used for self calibration.

In some aspects, a more complex planar bend (e.g., a circular loop), or a second bend in an orthogonal plane may provide increased accuracy. FIG. 7A is a diagrammatic perspective view that illustrates a more general implementation of a fixed fiber bend that may be used for self calibration. As shown in FIG. 7A, two complete, circular, orthogonal, intersecting optical fiber loops 730a,730b are placed in an optical fiber sensor 732. The curvilinear coordinate system s(t) is illustratively defined at the fiber location at which the bend transitions from loop 730a to loop 730b. Sensed strain information from the cores in fiber 732 over the lengths of loops 730a,730b can provide increased strain information accuracy. The loops are illustrative of various predefined 3-D fiber shapes, and they may be held in place by various mechanical constraints (e.g., closely fitting NITINOL tubing, grooves in fittings as described above, etc.). Fittings 734 in the diagram illustrate the mechanical constraints that hold the fiber in its predefined shape.

An advantage of using such a fixed bend is that it provides a calibration reference for all other bends in fiber 702 without the complexities of moving one or more joints or positioning joints in a work piece and determining calibration information, which would typically be done as an action during manufacturing. In addition, the calibration between the fiber base reference frame and the mechanical reference frame may be performed at startup each time the mechanism is used (e.g., for interchangeable kinematic robot arms, such as minimally invasive surgical instruments). Consequently, the calibration information does not need to be stored in a memory for later use as described above. Also, if the fiber bend is held in place in the fixture by friction (rather than by gluing, for example), then calibration at each shape sensing system startup can compensate for any fiber slippage within the fixture that has occurred. Further, the known curvature pattern of the planar bend in the fixture can be used as a sensor system self-test by comparing expected to actual results.

Figure 7B:
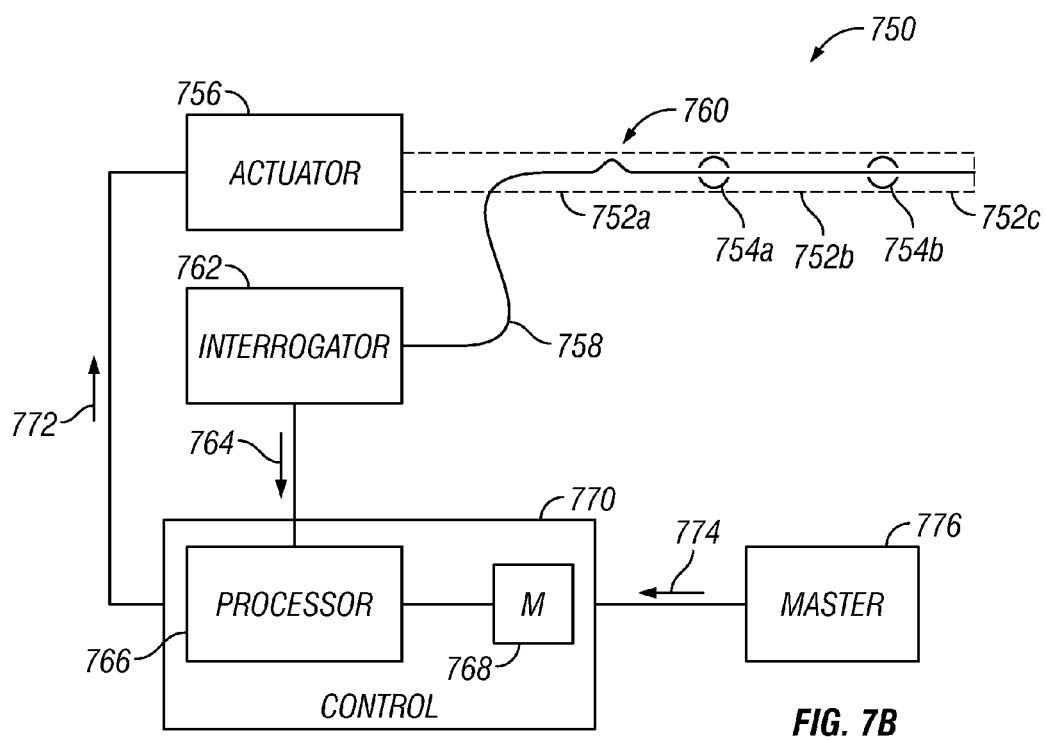
FIG. 7B is a schematic view of an illustrative kinematic chain and associated shape sensing, calibration, and control systems.

FIG. 7B is a schematic view of an illustrative kinematic chain 750 and associated shape sensing and control systems. Kinematic chain 750 includes three links 752a (proximal), 752b (middle), and 752c (distal) in series. The links are coupled by joints 754a (proximal) and 754b (distal). Servo actuator system 756 controls the link movements around the joints. A shape sensing optical fiber 758, as described above, is associated with kinematic chain 700 and runs through or along each of the links and joints. A predefined bend 760, as described above, is placed in a portion of fiber 758 associated with link 752a. An optical fiber shape sensing system interrogator unit 762, as described above, determines strain information from fiber 758, including bend 760. The strain information 764 from interrogator 762 is received by electronic data processor 766, which determines, e.g., self calibration information for kinematic chain 750 as described above. The calibration information is stored in memory 768. Processor 766 and memory 768 are components of control system 770 for kinematic chain 750. Control system 770 sends commands 772 to actuator unit 756 to direct movement of the links 752. Thus a closed loop control is established by the optical fiber shape sensing system determining a shape of kinematic chain 750, self calibrated as described herein, and control system 770 commanding actuator unit 756 to move the links based on the shape information. Further, control system 770 may receive user commands 774 from master control 776 to move kinematic chain 750 to a desired pose (e.g., teleoperation), and the shape sensing system provides feedback to control system 770 about kinematic chain 750's actual pose so that control system 770 may provide additional commands if necessary to place kinematic chain 750 in the desired pose.

In a further aspect, it is possible to combine joint level calibration and self calibration as described above. Referring to FIG. 7B, for example, a self calibration may be performed at system startup or when an interchangeable kinematic chain is coupled to actuator unit 756. Then, using commands stored in memory 768, control system 770 may command kinematic chain 750 to move to perform joint level calibration as described above. The calibration information associated with the joint level calibration is then stored in memory 768 in addition to the stored self calibration information.

Application to Minimally Invasive Surgical Systems

Optical fiber shape sensor calibration as described herein may have various applications. One noteworthy application is for minimally invasive surgical instruments, which require extremely precise control of position and orientation within a patient.

Figure 8:
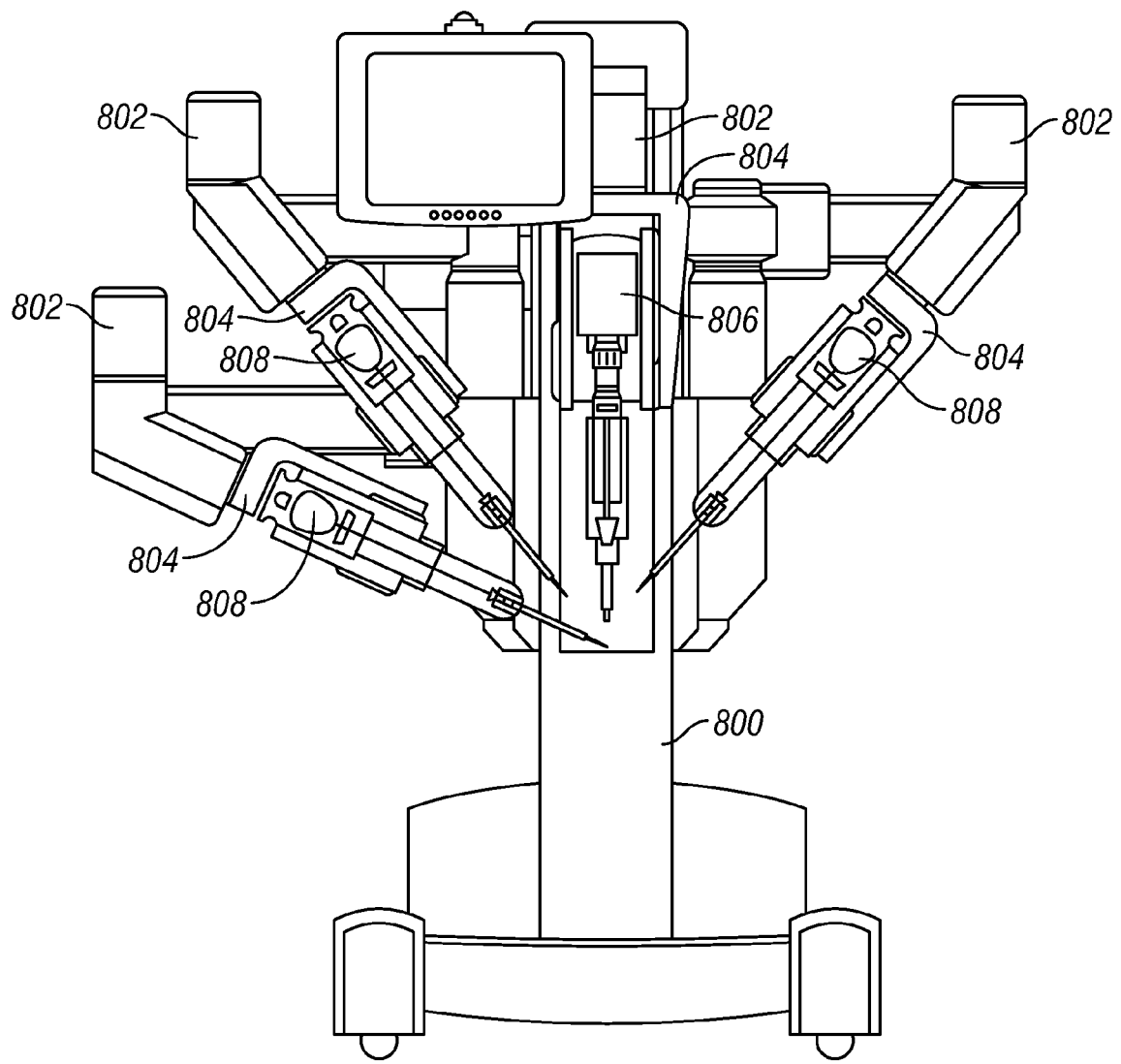
FIG. 8 is a diagrammatic view of a portion of a surgical robotic system.

The da Vinci® S™ HD™ Surgical System (Model No. IS2000) is manufactured by Intuitive Surgical, Inc., Sunnyvale, Calif. FIG. 8 is a diagrammatic view of a da Vinci® S™ HD™ patient side cart 800, showing passive jointed set up arms 802, actively controlled jointed instrument manipulators 804, an endoscopic camera 806, and actively controlled jointed surgical instruments 808. The following disclosure describes possible implementations on a surgical system similar to the da Vinci® S™ HD™ Surgical System, which illustrates how implementations may be carried out in various surgical and other systems.

In some aspects, instruments 808 may be modified to include a fiber optic shape sensor as described herein. A shape sensing interrogator is added to the surgical system, and the control system is modified to accommodate the shape sensing data. In some aspects, joint level and 3-D calibration may be done when the instruments 808 are manufactured. The calibration information is stored in an electronic memory for each instrument, in a manner similar to the way instrument data (e.g., type of instrument, number of uses, etc.) is currently stored. In other aspects, each instrument may have a self-calibration feature as described above. For example, link 700 (FIG. 7) or link 752a (FIG. 7B) are illustrative of the elongate shaft of instruments 800.

Figure 9:
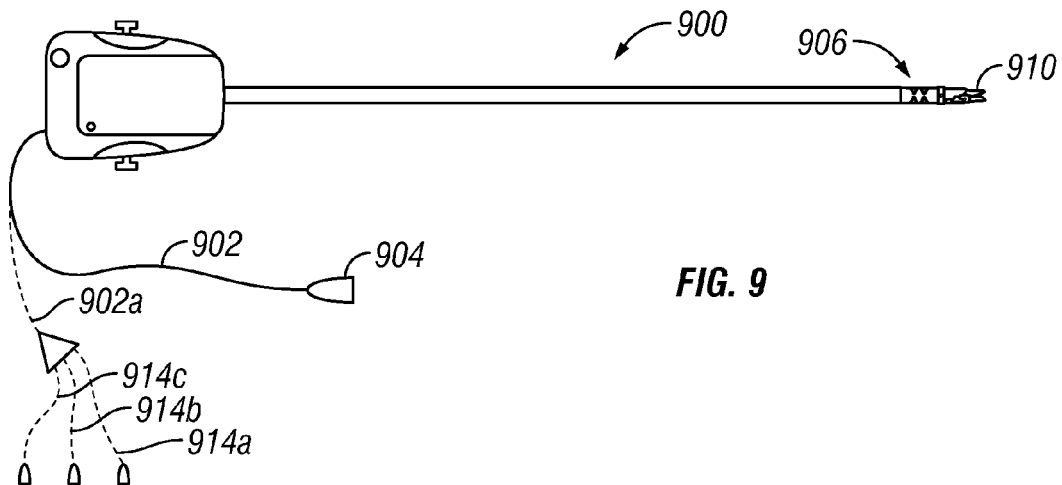
FIG. 9 is a diagrammatic plan view of a minimally invasive surgical instrument.
Figure 9A:
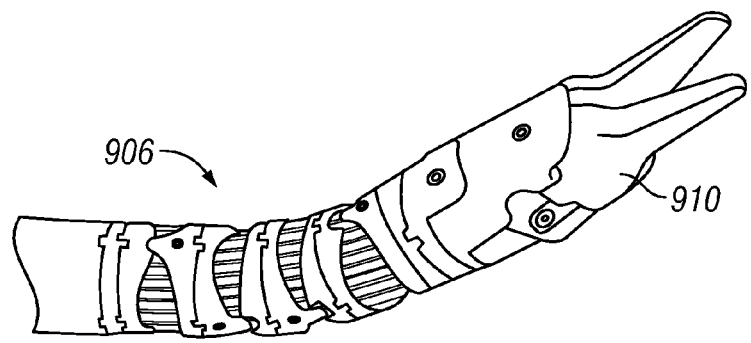
FIG. 9A is a view of a wrist mechanism.
Figure 9B:
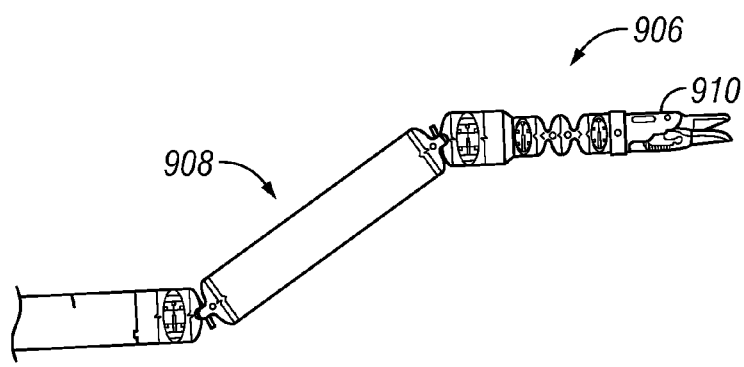
FIG. 9B is a view of a wrist mechanism and a parallel motion mechanism.

FIG. 9 is a diagrammatic plan view of a minimally invasive surgical instrument 900 used in the da Vinci® S™ HD™ system, which may be modified in accordance with aspects of the invention. Instrument 900 is illustrative of various similar instruments that may be used in various surgical and other systems. In accordance with aspects described herein, a multicore shape sensing optical fiber 902 may be embedded in instrument 900. Coupling 904 is used to couple fiber 902 to an optical fiber strain interrogation unit (see e.g., FIGS. 5, 6, and 7B). In some aspects, joint level calibration information as described above could be determined when the instrument is installed on a manipulator. Since instrument changes require the instrument be inserted into a cannula prior to insertion into a patient, such real time joint level calibration may not be practical. In some situations, however, the cannula may serve as a jig that straightens the instrument joints, and so calibration information may be obtained/updated at the time the joint passes through the cannula. In some aspects, however, joint level calibration is done during manufacturing, or before insertion into a patient, and the calibration information is stored in a memory in the instrument to be read by the surgical system's control system during operation, as described above. In some aspects, the shape sensor may be used to sense the orientation of a 2-DOF flexible wrist mechanism 906. FIG. 9A shows wrist mechanism 906 in more detail. Wrist mechanism 906 is illustrative of various other mechanisms, including flexible instruments, whose orientation and/or position may be sensed. FIG. 9B shows a combination of a wrist mechanism 906 and a parallel motion mechanism 908, which allows the position of end effector 910 to be changed without changing orientation. Parallel motion mechanism 908 is described in more detail in U.S. Patent Application Pub. No. US 2008/0065102 A1 (tiled Jun. 13, 2007) (disclosing "Surgical Instrument with Parallel Motion Mechanism"), which is incorporated herein by reference. In some instances the shape sensing optical fiber 902 may be routed through the center of wrist mechanism 906 and parallel motion mechanism 908. In other instances, optical fiber 902 may be routed at or near the outer surfaces.

FIG. 9 also illustrates that a multicore fiber may be coupled to an interrogation unit using three single core fibers. An alternate embodiment of fiber 902 is shown as fiber 902a. As shown, a splitter 912 is placed at the proximal end of multi-core fiber 902a, and three single core fibers 914a-914c are used to couple each core in fiber 902a to an optical coupling on an interrogation unit.

I claim:

1. A method of calibrating an optical fiber shape sensor, comprising:
   sensing strain in a segment of a multicore optical fiber associated with a kinematic chain;
   defining a fiber reference frame for the fiber;
   defining a kinematic chain reference frame for the kinematic chain;
   determining a calibration relationship between the fiber reference frame and the kinematic chain reference frame; and
   storing the calibration relationship in a memory.

2. The method of claim 1, wherein defining a fiber reference frame comprises:
   determining local bend information at each of a plurality of locations in the segment;
   wherein the local bend information at each location is determined in a two-dimensional reference frame;
   wherein the two-dimensional reference frame at each location is normal to the fiber; and
   wherein all two-dimensional reference frames are oriented in the same way with reference to the same core in the multicore fiber.

3. The method of claim 1 further comprising:
   positioning the kinematic chain in a known pose to create local bend in the fiber.

4. The method of claim 1 further comprising:
   rotating a joint in the kinematic chain with an actuator to create local bend in the fiber.

5. The method of claim 4:
   wherein the act of sensing strain occurs as the joint rotates.

6. The method of claim 1 further comprising:
   positioning the kinematic chain in a jig to create local bend in the fiber.

7. The method of claim 1 further comprising:
   positioning the fiber in a fixture associated with the kinematic chain to create the local bend in the fiber.

8. The method of claim 1, wherein determining the calibration relationship comprises:
   determining a two-dimensional rotational matrix that is used to transform bend information sensed in the fiber into bend information for a joint in the kinematic chain.

9. The method of claim 1, wherein determining the calibration relationship comprises:
   determining a three-dimensional matrix that is used to transform position and orientation information sensed in the fiber into position and orientation information for a link in the kinematic chain.

10. The method of claim 1 further comprising:
    determining a start location along the fiber at which strain begins to be sensed for the bend and an end location along the fiber at which strain stops being sensed for the bend; and
    defining a bend segment between the start location and the end location.

11. The method of claim 10 further comprising:
    adjusting either or both the start location and the end location to account for the fiber sliding in relation to a portion of the kinematic chain.

12. The method of claim 1 further comprising:
    determining an offset of the fiber from a centerline of the kinematic chain.

13. A method of calibrating an optical fiber shape sensor, comprising:
    positioning a first link in a kinematic chain at a plurality of angles with reference to a second link in the kinematic chain;
    interrogating a segment of a shape sensing optical fiber that extends between the first link and the second link for shape information at each of the plurality of angles;
    producing calibration information by correlating the shape information with a reference frame associated with the kinematic chain; and
    storing the calibration information in a memory.

14. The method of claim 13:
    wherein positioning the first link comprises moving the first link with an actuator.

15. The method of claim 13:
    wherein positioning the first link at a plurality of angles comprises sweeping the first link through an arc; and
    wherein interrogating the segment of the optical fiber for shape information comprises sampling the shape information during the sweeping.

16. The method of claim 13:
    wherein producing calibration information comprises determining an origin of a curvilinear coordinate system for the optical fiber.

17. The method of claim 13:
    wherein producing calibration information comprises correlating a bend axis of the optical fiber with a joint axis between the first link and the second link.

18. The method of claim 13:
    wherein producing calibration information comprises defining a bend angle of a joint between the first link and the second link based on local curvature information at each sensed local location in a bend of the fiber associated with the joint.

19. The method of claim 13:
    wherein producing calibration information comprises defining a location of the optical fiber at which a bend in the optical fiber starts.

20. The method of claim 13:
    wherein producing calibration information comprises defining a location of the optical fiber at which a bend in the optical fiber ends.

21. The method of claim 13:
    wherein producing calibration information comprises determining an offset of the optical fiber from a centerline of the kinematic chain.

22. A method of calibrating an optical fiber shape sensor, comprising:
    interrogating a segment of a shape sensing optical fiber for shape information that is associated with a predefined bend shape in the segment of the optical fiber;
    producing calibration information by correlating the shape information with a reference frame associated with a kinematic chain; and
    storing the calibration information in a memory.

23. The method of claim 22:
    wherein producing calibration information comprises determining an origin of a curvilinear coordinate system for the optical fiber.

24. The method of claim 22:
    wherein producing calibration information comprises defining a location of the optical fiber at which a bend in the optical fiber starts.

25. The method of claim 22:
wherein producing calibration information comprises defining a location of the optical fiber at which a bend in the optical fiber ends.

26. An optical fiber shape sensor calibration apparatus comprising:
an optical fiber strain interrogator, wherein the optical fiber strain interrogator senses strain in a segment of a multi-core optical fiber associated with a kinematic chain; and
an automated data processor, wherein the automated data processor determines a calibration relationship between a reference frame defined for the optical fiber and a reference frame defined for the kinematic chain, and wherein the automated data processor stores the calibration relationship in a memory.

27. The calibration apparatus of claim 26:
wherein the automated data processor determines local bend information at each of a plurality of locations in the segment;
wherein the local bend information at each location is determined in a two-dimensional reference frame;
wherein the two-dimensional reference frame at each location is normal to the fiber; and
wherein all two-dimensional reference frames are oriented in the same way with reference to the same core in the multicore fiber.

28. The calibration apparatus of claim 26 further comprising:
an actuator coupled to move the kinematic chain, wherein the actuator rotates a joint in the kinematic chain to create local bend in the fiber.

29. The calibration apparatus of claim 26 further comprising:
an actuator coupled to move the kinematic chain;
wherein the actuator rotates a joint in the kinematic chain to create local bend in the fiber;
wherein the segment of a multicore optical fiber is associated with the joint; and
wherein the optical fiber strain interrogator senses strain in the segment of a multicore optical fiber as the joint rotates.

30. The calibration apparatus of claim 26 further comprising:
a calibration jig;
wherein the calibration jig is configured to position the kinematic chain to create local bend in the fiber.

31. The calibration apparatus of claim 26 further comprising:
a fixture associated with the kinematic chain;
wherein the fixture is configured to position the kinematic chain to create local bend in the fiber.

32. The calibration apparatus of claim 26:
wherein determining a calibration relationship comprises determining a two-dimensional rotational matrix that is used to transform bend information sensed in the fiber into bend information for a joint in the kinematic chain.

33. The calibration apparatus of claim 26:
wherein determining a calibration relationship comprises determining a three-dimensional matrix that is used to transform position and orientation information sensed in the fiber into position and orientation information for a link in the kinematic chain.

34. The calibration apparatus of claim 26:
wherein determining a calibration relationship comprises determining a start location along the fiber at which strain begins to be sensed for the bend, determining an end location along the fiber at which strain stops being sensed for the bend, and defining a bend segment between the start location and the end location.

35. The calibration apparatus of claim 34:
wherein determining a calibration relationship further comprises adjusting either or both the start location and the end location to account for the fiber sliding in relation to a portion of the kinematic chain.

36. The calibration apparatus of claim 26:
wherein determining a calibration relationship comprises determining an offset of the fiber from a centerline of the kinematic chain.

37. An optical fiber shape sensor calibration apparatus comprising:
an actuator coupled to position a first link in a kinematic chain at a plurality of angles with reference to a second link in the kinematic chain;
an optical fiber strain interrogator, wherein the optical fiber strain interrogator interrogates a segment of an optical fiber that extends between the first link and the second link for shape information at each of the plurality of angles; and
an automated data processor, wherein the automated data processor produces calibration information by correlating the shape information with a reference frame associated with the kinematic chain, and wherein the automated data processor stores the calibration relationship in a memory.

38. The calibration apparatus of claim 37:
wherein the actuator sweeps the first link through an arc as the actuator positions the first link at the plurality of angles; and
wherein the optical fiber strain interrogator interrogates the segment of the optical fiber by sampling the shape information as the actuator sweeps the first link through the arc.

39. The calibration apparatus of claim 37:
wherein producing calibration information comprises determining an origin of a curvilinear coordinate system for the optical fiber.

40. The calibration apparatus of claim 37:
wherein producing calibration information comprises correlating a bend axis of the segment of the optical fiber with a joint axis between the first link and the second link.

41. The calibration apparatus of claim 37:
wherein producing calibration information comprises defining a bend angle of a joint between the first link and the second link based on local curvature information at each sensed local location in a bend of the fiber associated with the joint.

42. The calibration apparatus of claim 37:
wherein producing calibration information comprises defining a location of the optical fiber at which a bend in the optical fiber starts.

43. The calibration apparatus of claim 37:
wherein producing calibration information comprises defining a location of the optical fiber at which a bend in the optical fiber ends.

44. The calibration apparatus of claim 37:
wherein producing calibration information comprises determining an offset of the optical fiber from a centerline of the kinematic chain.

45. An optical fiber shape sensor calibration apparatus comprising:
an optical fiber strain interrogator, wherein the optical fiber strain interrogator interrogates a segment of a shape sensing optical fiber for shape information that is associated with a predefined bend shape in the segment of the optical fiber; and an automated data processor, wherein the automated data processor produces calibration information by correlating the shape information with a reference frame associated with a kinematic chain, and wherein the automated data processor stores the calibration relationship in a memory.

46. The calibration apparatus of claim 45:

wherein producing calibration information comprises determining an origin of a curvilinear coordinate system for the optical fiber.

47. The calibration apparatus of claim 45:

wherein producing calibration information comprises defining a location of the optical fiber at which a bend in the optical fiber starts.

48. The calibration apparatus of claim 45:

wherein producing calibration information comprises defining a location of the optical fiber at which a bend in the optical fiber ends.

* * * * *